(12) United States Patent
Teutenberg

(10) Patent No.: US 9,044,866 B2
(45) Date of Patent: Jun. 2, 2015

(54) LABORATORY SYSTEM

(75) Inventor: Reinhard Teutenberg, Unna (DE)

(73) Assignee: THYSSENKRUPP POLYSIUS AKTIENGESELLSCHAFT, Beckum (DE)

( * ) Notice: Subject to any disclaimer, the term of this patent is extended or adjusted under 35 U.S.C. 154(b) by 606 days.

(21) Appl. No.: 12/681,849

(22) PCT Filed: Sep. 22, 2008

(86) PCT No.: PCT/EP2008/062639
§ 371 (c)(1),
(2), (4) Date: Apr. 6, 2010

(87) PCT Pub. No.: WO2009/049995
PCT Pub. Date: Apr. 23, 2009

(65) Prior Publication Data
US 2010/0219968 A1   Sep. 2, 2010

(30) Foreign Application Priority Data

Oct. 10, 2007  (DE) .......................... 10 2007 048 684

(51) Int. Cl.
*B25J 19/06*    (2006.01)
*B25J 5/02*     (2006.01)
*F16P 3/14*     (2006.01)
(Continued)

(52) U.S. Cl.
CPC .. *B25J 19/06* (2013.01); *B25J 5/02* (2013.01); *F16P 3/14* (2013.01); *G01N 35/026* (2013.01); *G01N 35/04* (2013.01); *G01N 2035/041* (2013.01); *G01N 2035/0481* (2013.01); *F16P 3/142* (2013.01); *F16P 3/147* (2013.01)

(58) Field of Classification Search
USPC .......................... 340/686.6, 539.15, 664, 679; 422/63–67
See application file for complete search history.

(56) References Cited

U.S. PATENT DOCUMENTS 3,696,368 A * 10/1972 Kauffman ..................... 340/553
4,391,774 A *  7/1983 Dupain ........................... 422/63
4,636,137 A *  1/1987 Lemelson ..................... 414/730
(Continued)

FOREIGN PATENT DOCUMENTS

DE       3208901 A1   9/1983
DE       8717574 U1   7/1989
(Continued)

*Primary Examiner* — Julie Lieu
(74) *Attorney, Agent, or Firm* — Gifford, Krass, Sprinkle, Anderson & Citkowski, P.C.

(57) ABSTRACT

The laboratory system according to the invention substantially comprises a transport device for samples, at least one handling device for preparing, analyzing and/or processing samples, at least one movable manipulation device for handling the samples in the region of a handling device, the manipulation device being configured for the transfer of the sample between the transport device and the handling device, and a monitoring system which travels with the manipulation device for maintaining a safety distance. The manipulation device can be moved between at least two handling devices and the monitoring system is a monitoring system which travels with the manipulation device and which is formed by a camera for producing remote images and/or a location system having at least one transmitter and at least one receiver. The receiver of the location system is mounted on the movable transport device and is constructed in such a manner that it produces an alarm signal if the at least one transmitter falls below a minimum distance relative to the receiver.

7 Claims, 6 Drawing Sheets

Figure 1:
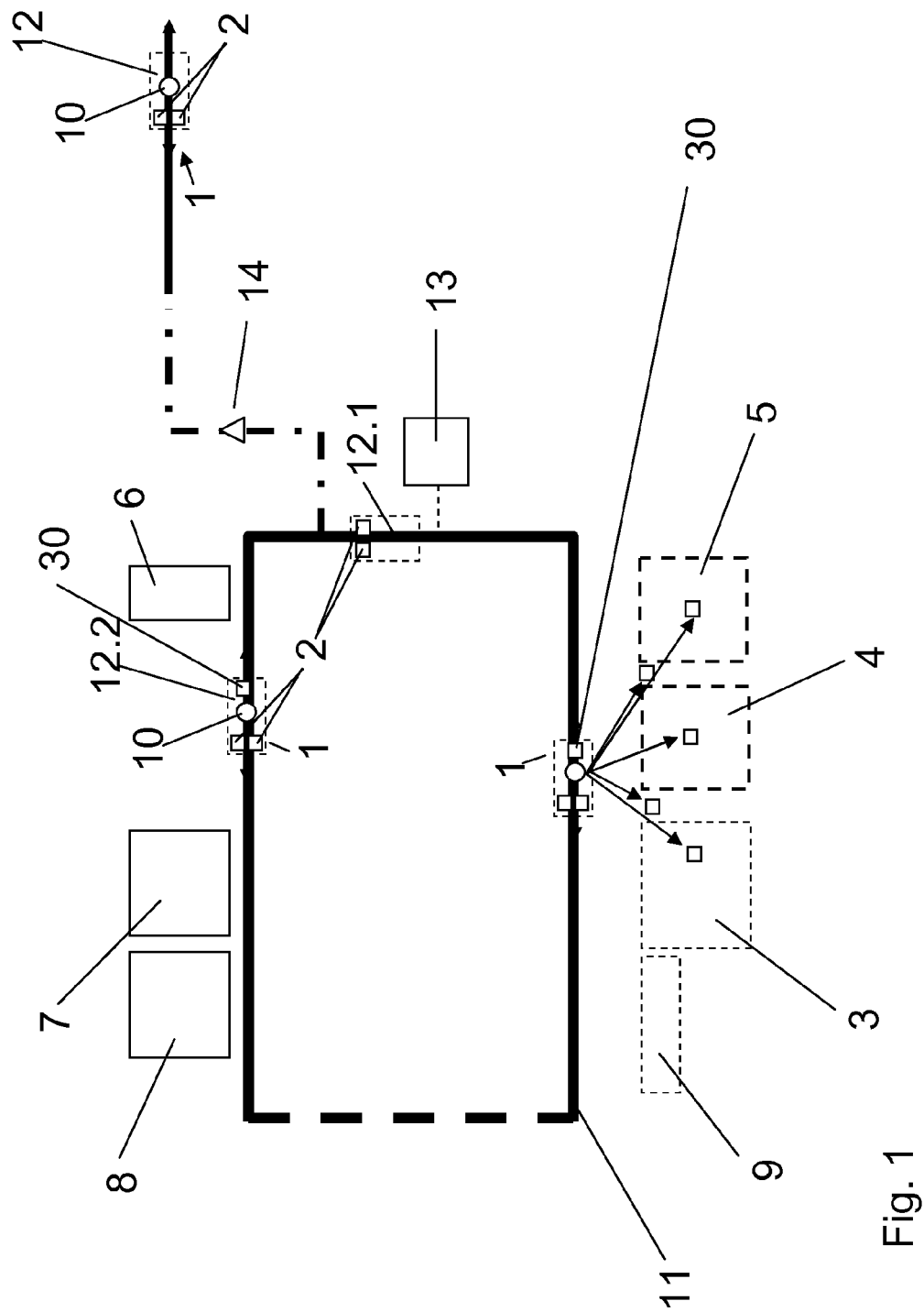

(51) Int. Cl.
  *G01N 35/04* (2006.01)
  *G01N 35/02* (2006.01)

(56) References Cited

U.S. PATENT DOCUMENTS

| | | | | |
|---|---|---|---|---|
| 4,652,205 | A * | 3/1987 | Ross et al. | 700/259 |
| 4,661,797 | A * | 4/1987 | Schmall | 340/561 |
| 4,849,175 | A * | 7/1989 | Dupain et al. | 422/63 |
| 5,047,752 | A * | 9/1991 | Schorn | 340/680 |
| 5,141,364 | A * | 8/1992 | Degen et al. | 405/240 |
| 6,082,797 | A * | 7/2000 | Antonette | 294/103.1 |
| 6,778,092 | B2 * | 8/2004 | Braune | 340/679 |
| 7,628,954 | B2 * | 12/2009 | Gomm et al. | 422/63 |
| 7,641,402 | B2 * | 1/2010 | Kocanda et al. | 396/427 |
| 2002/0175825 | A1 * | 11/2002 | Clerk et al. | 340/686.6 |
| 2005/0058574 | A1 * | 3/2005 | Bysouth et al. | 422/63 |
| 2005/0215256 | A1 * | 9/2005 | Tsutazawa et al. | 455/437 |
| 2005/0279584 | A1 * | 12/2005 | Reuter et al. | 187/249 |
| 2006/0169887 | A1 * | 8/2006 | Yamaguchi et al. | 250/288 |
| 2006/0224030 | A1 * | 10/2006 | Euzen et al. | 585/467 |
| 2007/0005169 | A1 | 1/2007 | Rohnart et al. | |
| 2007/0199108 | A1 * | 8/2007 | Angle et al. | 901/17 |
| 2008/0018472 | A1 * | 1/2008 | Dasilva et al. | 340/572.4 |
| 2009/0301522 | A1 * | 12/2009 | Abehasera et al. | 134/18 |
| 2010/0269555 | A1 * | 10/2010 | Theis et al. | 72/4 |
| 2014/0124332 | A1 * | 5/2014 | Hayduchok et al. | 198/347.2 |

FOREIGN PATENT DOCUMENTS

| | | |
|---|---|---|
| DE | 29520515 U1 | 9/1996 |
| DE | 19930019 A1 | 1/2001 |
| DE | 20006549 U1 | 8/2001 |
| DE | 20120700 U1 | 4/2003 |
| DE | 20310903 U1 | 9/2003 |
| DE | 10344284 A1 | 5/2005 |
| DE | 102005063193 A1 | 7/2007 |
| DE | 102006002704 A1 | 8/2007 |
| DE | 102006015889 A1 | 10/2007 |
| EP | 0179252 A2 | 4/1986 |
| EP | 0633207 A1 | 1/1995 |

\* cited by examiner

LABORATORY SYSTEM

The invention relates to a laboratory system having a transport device for samples, at least one handling device for preparing, analysing and/or processing samples, at least one movable manipulation device for handling the samples in the region of a handling device and a monitoring system which travels with the manipulation device for maintaining a safety distance.

From the field of cement production, a laboratory system is known in which the different handling devices are arranged around a robot which is arranged at the centre. The robot transfers the samples between the handling devices and guides the samples to the individual handling devices. The samples are generally transported by means of a sample carrier which is, for example, normally a cup or a steel ring. The sample material is either located loose in the cup or pressed into the steel ring.

The metering of the sample material from the sample carrier (cup) is also carried out by the robot. Such a central robot is, however, relatively expensive and is potentially dangerous to humans owing to its large operating range and kinematics (significant forces and accelerations) with the result that adequate safety enclosures are required. Furthermore, the installation possibilities for the individual handling devices are limited by the central arrangement of the robot.

EP-A-0 633 207 proposes a laboratory system in which the transport of the samples to the individual handling devices is carried out by means of a continuously rotating conveyor belt. The conveyor belt can be stopped by means of stop devices in order to move a sample carrier in a handling device into a predetermined stop position. A manipulation device which is associated with the handling device then transports a sample carrier from the stop position to the respective handling device and back.

Although, in this laboratory system, the arrangement of the individual handling devices is substantially more variable and an expensive central robot can be dispensed with, the system is still relatively complex.

In practice, a laboratory system is further known in which the samples are transported with a self-propelling robot which is provided, for example, with a laser scanner in order to be able to move around obstacles.

DE 200 06 549 U1 discloses a device for automatically carrying out chemical or biological processes in sample vessels. In this instance, the sample vessels are transported to a handling device by means of a belt conveyor. The end positions of a conveyor carriage which can be reached by the belt conveyor are monitored by means of sensors. By means of a manipulation device which is provided in the region of the handling device, the sample vessels are transferred between the conveyor carriage and handling device.

DE 199 30 019 A1 describes a device for controlling the transport of cleaning material on a transport path. The spacings and the orientation of the cleaning material on the transport path are monitored by means of a camera and an image processing system.

The control of a conveying technology by means of computer-supported image recognition is further known from DE 10 2006 015 689 A1, DE 10 2006 002 704 A1 and DE 10 2005 063 193 A1.

In DE 203 10 903 U1 and DE 87 17 574 U1, optoelectronic elements are further used for position or object recognition in conveying systems.

DE 295 20 515 U1 describes a transport system in which the carriage has a CCD camera for recognition of the guiding path. Finally, DE 201 20 700 U1 relates to a bottle transfer system which has a monitoring device having a camera system and image evaluation.

The object of the invention is to provide a laboratory system which allows man and machine to work in parallel, without complex safety enclosures being required.

This object is achieved according to the invention by the features of claim 1.

The laboratory system according to the invention substantially comprises a transport device for samples, at least one handling device for preparing, analysing and/or processing samples, at least one movable manipulation device for handling the samples in the region of a handling device, the manipulation device being configured for the transfer of the sample between the transport device and handling device and a monitoring system which travels with the manipulation device for maintaining a safety distance. The manipulation device can be moved between at least two handling devices and the monitoring system is a monitoring system which travels with the manipulation device and which is formed by a camera for producing remote images and/or a location system having at least one transmitter and at least one receiver. The receiver of the location system is mounted on the movable transport device and is constructed in such a manner that it produces an alarm signal if the at least one transmitter falls below a minimum distance relative to the receiver. The camera is secured to the manipulation device or also to the transport device. A monitoring system is used if there is a potential danger to humans from the manipulation device which is mounted on the movable transport device.

Owing to the monitoring system which preferably comprises both the camera and the location system, it is possible for man and machine to work in parallel in relatively close proximity, without complex safety enclosures which limit the freedom of movement being required.

The dependent claims relate to further developments of the invention.

According to another configuration of the invention, the monitoring system further comprises an electrical current and/or power monitoring device which monitors current and/or power values of the manipulation device.

In addition to the movable manipulation devices, it is further conceivable for at least one handling device to also be constructed so as to be movable, whereby the flexibility of the laboratory system can be further increased.

The term sample is intended to refer to a sample carrier which comprises, for example, a cup with sample material, a steel ring with sample material pressed in, empty cups, empty steel rings and various containers of different sizes for sample material. The sample material is, for example, transported loose in cups or containers. However, it is also conceivable for the sample material to be pressed into a steel ring after suitable preparation.

The manipulation device can also be configured in such a manner that it can meter the sample material from the sample carrier, in particular the cup, in a handling device.

The transport devices can move from one location to another optionally in a self-propelled manner or on a predetermined transport path, in particular a track.

The transport paths may extend in different spaces and/or on different planes and can be coupled to each other in any manner desired. According to a specific configuration, the manipulation device can be moved together with one or more samples on the transport device. There may also be provision for there further to be one or more transport devices which transport only one or more samples.

According to a preferred configuration, the transport devices have an individual energy supply, in particular a low-voltage system and can be constructed so as to be self-propelled. In addition, the transport device can supply the manipulation device to be carried or the handling device with electrical energy.

Advantageously, the transport path is constructed in a modular manner and can be simply expanded in any manner desired. To this end, it is not necessary to install any other electrical components (apart from the rails). According to another configuration of the invention, the transport system comprises at least a first transport path and a second transport path which is arranged offset in a vertical direction, a lifting device for the transport devices being provided between the first and second transport path. In this manner, the handling devices can be arranged on different levels or floors. A plurality of paths can also extend parallel and be combined in any manner desired.

Figure 2:
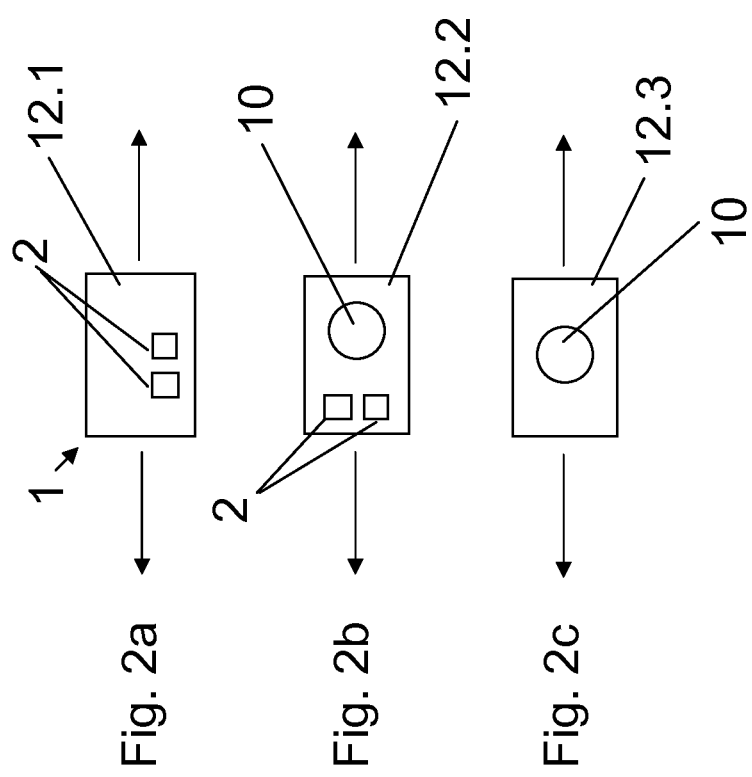
Figure 3:
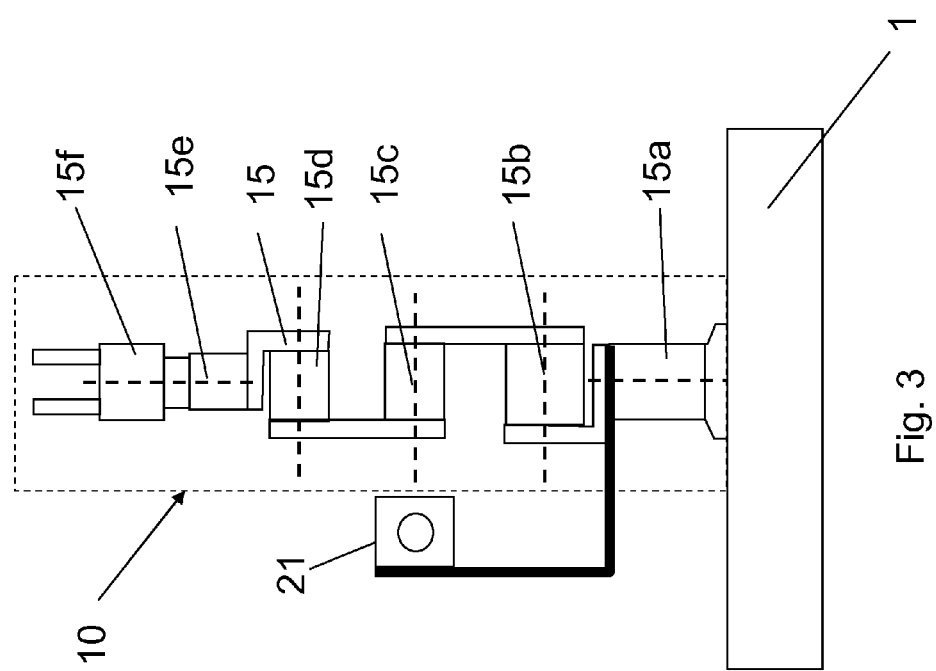
Figure 4:
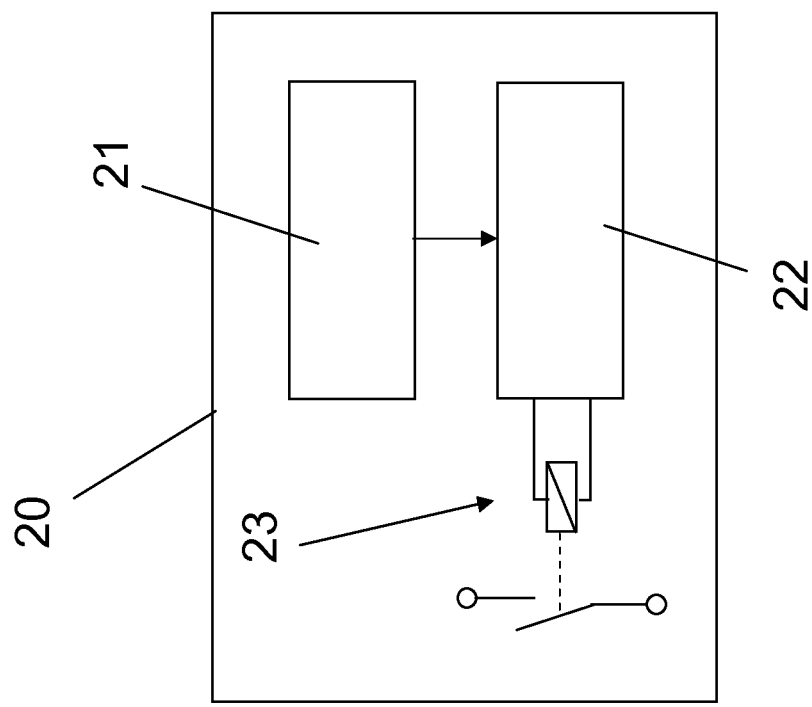
Figure 5:
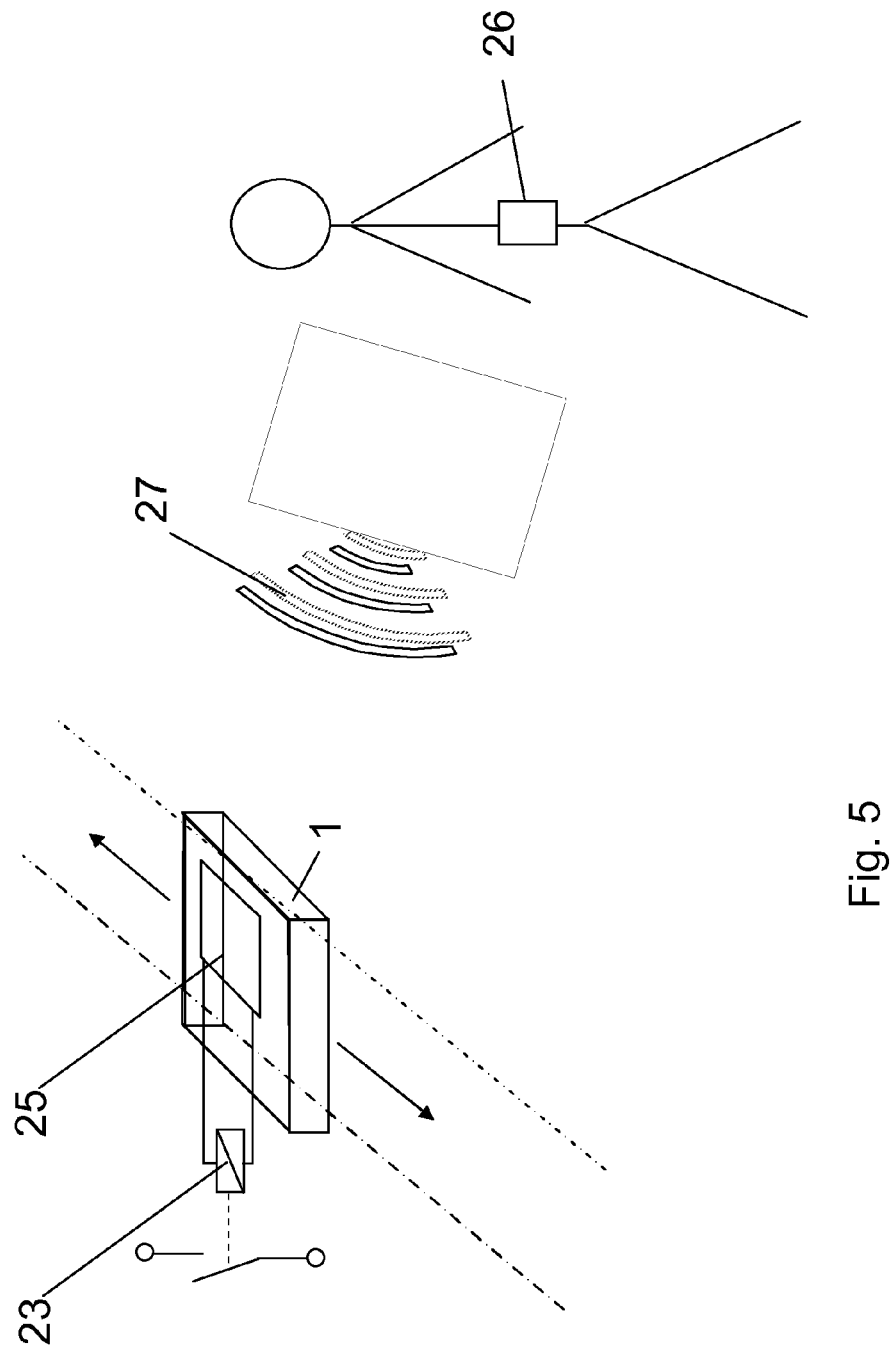
Figure 6:
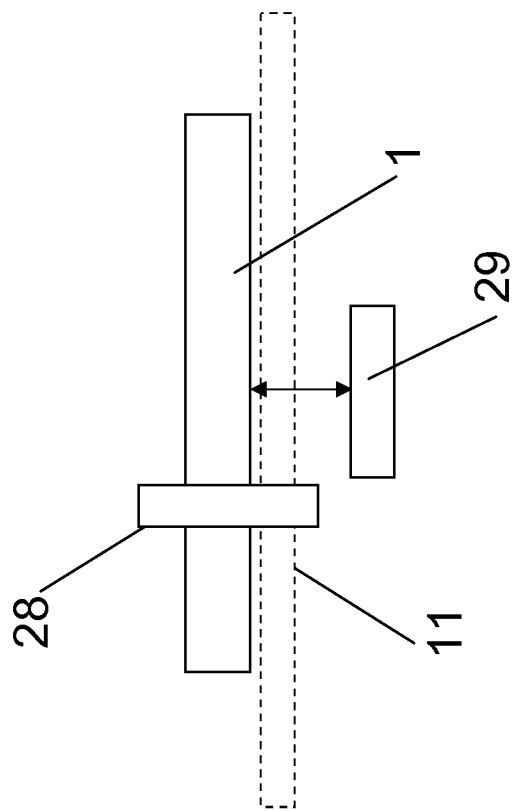

Further advantages and configurations of the invention will be described in greater detail below with reference to the description and the drawings, in which:

FIG. 1 is a schematic block diagram of the laboratory system,

FIGS. 2a-2c are schematic illustrations of various configurations of the transport devices (shuttle), FIG. 3 is a schematic illustration of a transport device having a manipulation device and monitoring device having a camera, FIG. 4 is a schematic illustration of the monitoring device having a camera, FIG. 5 is a schematic illustration of the location system, and FIG. 6 is a schematic illustration of a positioning unit and a loading station.

The laboratory system illustrated in FIG. 1 substantially comprises a transport device 1 for samples 2, a plurality of handling devices 3 to 9 and at least one manipulation device 10 for handling the samples 2 in the region of a handling device.

The term sample is intended to refer to a sample carrier which comprises, for example, a cup with sample material, a steel ring with sample material pressed in, empty cups, empty steel rings and various containers of different sizes for sample material. The sample material is, for example, transported loose in cups or containers. However, it is also conceivable for the sample material to be pressed into a steel ring after suitable preparation.

The transport devices (for example, a shuttle) are either constructed so as to be self-propelled or can be moved along a transport path 11, in particular a track.

The manipulation device 10 can either be moved on the transport path 11 or a second transport path between at least two of the handling devices 3 to 9. In the embodiment illustrated, the manipulation device 10 can be moved on the transport device together with one or more samples 2.

The manipulation device 10 is configured for the transfer of the sample 2 between the transport device 1 and one of the handling devices 3 to 9. The manipulation device 10 may comprise, for example, an appropriately constructed gripping arm 15 which can receive the sample or the sample carrier with the sample material and can optionally also meter the sample material from the sample carrier in the region of a handling device. The metering can be carried out by slowly tipping out the sample material. In order to improve the flow behaviour of the sample material, it would also be possible to additionally provide means which excite the gripper 15f of the manipulation device 10 or the gripper arm 15 with a high-frequency vibration.

According to a preferred embodiment, the laboratory system is constructed for preparing, analysing and/or processing samples of cement production and/or ore and mineral preparation. In this instance, the handling devices 3 to 9 are, for example, a tubular post receiving station 3, a mill/press 4, 5, a fineness measuring device 6, a spectrometer 7, a diffractometer 8 and a resetting system 9.

With reference to FIGS. 2a-2c, various configurations of the transport devices (shuttle) are illustrated. The transport device 1 (12.1) illustrated in FIG. 2a is constructed purely as a transport shuttle for one or more samples 2. The transport device 12.2 illustrated in FIG. 2b, in addition to transporting the samples 2, also serves to transport a manipulation device 10. The transport device 12.3 according to FIG. 2c is finally constructed purely as a manipulation shuttle and simply carries a manipulation device 10.

According to another configuration of the invention, the transport devices 1 have their own energy supply, in particular a low-voltage system. Consequently, the transport devices can also be constructed, for example, so as to be self-propelling. In addition, the transport device can also supply electrical energy to a manipulation device or a handling device (mounted on the transport device).

However, the electrical power supply of the transport devices and the manipulation device or the handling device can also be carried out via the transport path (for example, rail).

The transport path for the transport devices can be constructed as a rail track, it then advantageously being constructed in a modular manner so that it can be constructed with any shape and extent.

In order to achieve even greater flexibility of the path guiding, it would be possible to provide a first transport path and a second transport path which is arranged offset in a vertical direction, a lifting device 14 for the transport devices being provided between the first and the second transport path (FIG. 1). It is consequently possible to produce connections of paths on different levels.

Of course, in the context of the invention, any other construction steps for extending the transport path are conceivable and can be adapted to the respective laboratory conditions. With the above concept, free spatial configuration is possible since the handling devices can be positioned almost anywhere in spatial terms.

FIG. 3 illustrates a manipulation device 10 which is mounted on a transport device 1 and which can be moved therewith. The manipulation device is formed in this instance, for example, by a special gripper arm 15. Furthermore, in this instance, a camera 21 which is secured to the gripper arm for producing remote images is illustrated. However, the camera 21 can also be mounted on the movable transport device.

The gripper arm 15 is constructed in this instance as a scaleable lightweight arm and has a plurality of rotation and pivot units 15a, 15b, 15c, 15d and 15e, by means of which reconfigurable, modular robot structures can be produced. In addition, there is also an electrical gripper 15f. The individual drive modules (gripper and rotation/pivot units) can be mounted in a free and flexible manner with connection components to form an individual lightweight arm in the IP65 class of protection.

The operating range can be adapted to the application by free selection of the kinematic structure. The rotation and pivot units are moved, for example, by brushless servomotors with harmonic drive gears and already have a complete electronic power and control system, which allows positioning movement with gradient control and end position, voltage, current and temperature monitoring. Owing to the use of light and at the same time highly stable materials, the compact pivot units achieve an inherent mass/bearing load ratio which is better than 2:1. The power supply, the control possibilities and the universal communication interfaces can already be integrated so that only a cable is required for drive networking.

Since the drive components are provided with hollow shafts, the cabling can be guided internally and consequently in a protected manner. The 24V direct-current voltage is sufficient for the operation of the lightweight arm. The low energy requirement of the lightweight arm is advantageously met by the on-board power supply of the transport device. The control of the lightweight arm is carried out, for example, by means of an embedded controller on the basis of a single-board PC. A specific robot control system (known from industrial robots) is consequently not required.

The transport device 1 (construction with manipulation device 10) further has a monitoring device 20 which is formed in the embodiment according to FIG. 3 by a camera 21 for producing remote images.

The camera 21 may be, for example, a so-called TOF camera (Time-of-Flight camera). The TOF principle is based on the measurement of the light travel time. A light pulse is transmitted and measures the time which the light requires to return when it is reflected from an object. In this manner, for each pixel the spacing relative to an object can be established so that a three-dimensional structure of the scene is obtained.

The handling stations are approached by the transport device, the immediate vicinity of the respective handling station being captured as an image by the camera and a pattern being generated. The image capture is carried out at each handling station so that the working conditions for the manipulation device are captured and learnt. The respective image capture is first carried out without the devices being operated by operating personnel (so-called static image capture).

The camera can also be moved to capture the complete conditions. If the camera is secured to the handling device, it is automatically orientated in the operating direction of the manipulation device.

During automatic operation, the handling stations are approached as desired by the transport devices. In addition, the laboratory personnel are able to work in the same space as the handling stations. For manual access to the handling stations, the devices are generally switched into service or manual mode. Since it cannot be excluded that the personnel also access or are located in the working space of the manipulation unit, this working space is monitored by the camera. Prior to and during the implementation of the manipulation operations by the manipulation device, new image information is generated sufficiently quickly and compared with the static image taken. Deviations from the original images, for example, when personnel enter the monitoring region, are recognised sufficiently quickly and lead to the manipulation device being switched off.

To this end, the monitoring device 20 according to FIG. 4 has, in addition to the camera 21, an evaluation switch 22 which co-operates with a trip circuit 23 in order to switch off the manipulation device 10 if it falls below a predetermined safety distance.

It is thus possible to promptly detect persons in the operating region of the manipulation device or on the movement path of the transport device. Owing to the specially implemented evaluation method (differential image analysis), occurrences of falling below the minimum safety distance are quickly detected and movements of the manipulation device prevented for technical safety reasons. In addition, different safety zones can be set up so that, when persons approach, firstly only the speed of the manipulation device can be reduced. The warning and protection fields can be configured in a flexible manner.

In order to meet the requirements for co-operation of man and machine without safety partitions/protective fencing, it is also possible to provide, instead of or in addition to the monitoring device 20 with a camera, a location system having at least one transmitter and at least one receiver (see FIG. 5). In this instance, a receiver 25 is secured to the movable transport device 1 and is constructed in such a manner that it produces an alarm signal if at least one transmitter 26 falls below a minimum spacing relative to the receiver.

The location system makes provision for the laboratory personnel to carry the transmitters 26 which activate an alarm signal when approaching the receiver 25 which is fitted to the manipulation device or the transport device and, via a trip circuit 23, switch the manipulation device 10 into a powerless state for technical safety reasons. The region to be monitored can be adjusted in any manner desired and may, for example, comprise 1 m around the receiver. Carrying the transmitters 26 is compulsory for the laboratory personnel and can be monitored by means of an additional receiving unit in the region of the entrance (access control). This optional access control monitors the carrying of the transmitters by the personnel when passing through doors to the laboratory or laboratory building and activates an alarm, if necessary. In addition, coupling with automatic door locking is also possible.

The 3D location is based, for example, on microwave distance measurements or measurements of the run time differences of a radio signal 27 to various receivers. In comparison with the use of video systems, this technology requires no visual contact with the objects or persons to be monitored.

According to another configuration, the monitoring system may comprise an electrical current and/or power monitoring device, which monitors current and/or power values of the manipulation device 10. In particular, the drive currents or the total power of the manipulation device are monitored and evaluated. The current/power values are provided in a redundant state and, if the limit values are not adhered to, the drives are switched into a powerless state for technical safety reasons. The electrical energy of the manipulation unit can thus be limited, for example, to 80 W. Compliance with the limit values is monitored in this manner for technical safety reasons.

At least one of the three monitoring devices described above is used in the laboratory system so that indirect co-operation or parallel working of man and machine is possible without the conventional protection/safety enclosures. If a plurality of different monitoring devices are provided, the safety can be further increased.

Indirect co-operation means that the laboratory personnel may work in the same space where the automatic processes including the automatic manipulation are also being carried out. Different handling stations are involved in the automatic process but are also available for manual operation. It is now possible to operate operating stations manually at any time, whilst adjacent stations are at the same time involved in the automatic process.

As soon as the member of laboratory personnel approaches the danger point "automatic manipulation" or arrives at or reaches into the operating space of the manipulation device, the automatic manipulation is stopped. All technical aspects of safety are taken into consideration in this instance.

The working space of the manipulation device is not fixed in position and the monitoring of the working space must therefore be dynamic. The monitoring is consequently coupled to the transport device. Based on the transport device, the immediate vicinity is monitored for technical safety reasons.

The immediate vicinity is connected to the maximum range of the manipulation unit, and the monitoring region is adjusted accordingly.

The arrangement of the safety zones or the secured working regions requires neither complex installations nor complex operation. The level of complexity of automation is also low. Unlike the 2D scanners which are currently used or the Pilz Safety Eye, the complexity of the arrangement of the safety zones is consequently low. With the location system, it is also possible to monitor regions which cannot be detected optically (a person comes, for example, from a so-called dead zone, since the working region is blocked by the device to be operated).

The laboratory personnel can move safely and freely in the space and all the devices are readily accessible (no enclosures, no barriers). All commercially available laboratory manipulation stations can be positioned at any location freely in the space and do not have to be secured by safety enclosures.

Furthermore, it is possible for a manual and/or automatic manipulation (transport and/or handling of the samples) to be carried out selectively or simultaneously on one or more handling devices. The transport device and the handling of the samples with the manipulation device are advantageously provided at one side of the handling device, and the operating side at the other side of the handling device.

The manual manipulation may, for example, involve the laboratory personnel taking over the operation of the manipulation device, for example, the transfer from a transport device into the handling device. However, it is also conceivable for even the transport of a sample to the handling device to be carried out by an operator/person. The manual manipulation is allowed primarily by the fact that the system does not require any safety enclosures, such as protective doors.

In another configuration of the invention, the laboratory system is characterised by expandable requirement-orientated device logistics, one or more handling devices being constructed so as to be movable and being transported to precisely where they are required. There are consequently the following possibilities:

a) manipulation device on a transport device travels to a handling device;

b) samples are transported to a stationary handling device, to a movable manipulation device or to the operator;

c) handling devices travel to an operator or to a stationary or movable manipulation device.

Mobile handling devices may be, for example, specific metering systems, sample separators or other devices which are mounted on a transport device. The handling devices on the transport device are controlled in the same manner as the handling device by the embedded controller.

It is thereby possible to further optimise the workflow in the laboratory by means of the path reduction. For example, if a movable manipulation device is connected to one or more handling devices owing to high sample levels, the movable handling device can also travel and be operated in the operating region of the movable manipulation device. In addition, movable/mobile handling devices can be added in order to improve or accelerate the sample flow at a desired location. Furthermore, the mobile handling devices may also approach stationary handling devices.

The mobile handling units are considered to be mobile hardware service units. The mobile hardware service units can operate and be used locally in a specific environment but can also be requested by other automation cells. Consequently, different automation cells can access the same resources (hardware service) and use them as required in accordance with capacity. Each automation cell (one automation cell may comprise one or more handling devices or may be a complex automated device) knows usable resources and can request them. Consequently, an automation cell can be expanded dynamically upon request. It is also possible to couple new or available automated systems to a freely configurable system.

The mobile units are not necessarily associated with an automation cell. The mobile unit makes itself and consequently its service (hardware service) available. Each mobile unit is self-sufficient and may be provided in large numbers of its type, each independent unit being provided with the embedded controller. This allows data-technical laboratory networking, is automatically integrated into the environment provided (makes itself known) and controls the respective carried handling device or manipulation device.

The system consequently provides, in addition to the stationary handling devices which are approached and operated by a mobile handling device, variable and movable handling devices which can be used in any manner and can dynamically expand the system.

In another configuration of the invention (FIG. 6), the transport system has, along its transport path 11, one or more positioning units 28 at which the transport devices can be stopped at a precise point. The positioning units are provided primarily in the region of the handling devices and lifting devices in order to ensure precise handling of the samples and the transport devices.

Furthermore, charging stations 29 may be provided at which the electrical energy supply (in particular power capacitors or accumulators) of the transport devices can be charged.

The transport path constitutes the logical connection between individual handling devices (preparation, analyser, etc.) or automation cells (for example, laboratory automated system). This transport path is constructed in accordance with rules which support the individual processes and/or provide the handling devices or automation cells, for example, with samples.

The transport devices may additionally have a writable data storage device for the type of samples and/or the handling devices to be approached.

The transport device receives the data relating to the next handling device to be approached from the carried embedded controller. An external control system 13 manages all the possible tasks and is responsible for the sample logistics in the laboratory. The communication of the control system 13 with the embedded controller is carried out via a radio link (WLAN, Bluetooth). The tasks received by the embedded controller are evaluated in this instance by an embedded protocol handling device and transmitted to the transport device or the manipulation device. The embedded controller transmits new route information to the transport device and ultimately also permits onward travel. The embedded controller also controls the manipulation device. The stored movement programmes for the manipulation device are activated by the external control system 13. The external control system also knows the respective operating status of the handling device and takes this into consideration in the interaction of the manipulation device and handling device and when establishing the optimal route for the transport device.

The invention claimed is:

1. Laboratory system constructed for preparing, analysing and/or processing samples of cement production and/or ore and mineral preparation, said laboratory system comprising:
   at least two of the following handling devices for preparing, analysing and/or processing the samples: a tubular post receiving station, a mill, a press, a fineness measuring device, a spectrometer and a diffractometer;
   at least one of the two handling devices is constructed to be moveable and be transported to precisely where it is required;
   one or more transport devices for samples for transporting the samples loose or pressed in sample carriers between the at least two handling devices;
   at least one manipulation device with a gripper arm for handling the samples in the region of the handling devices, the manipulation device being mounted on the transport device, the transport device, at least one manipulation device with the gripper arm and samples moveable between at least the two handling devices along a transport path and configured for the transfer of the samples between the transport device and the handling device; and
   a monitoring system (30) for maintaining a safety distance, the monitoring system having an electrical current and/or power monitoring device which monitors current and/or power values of the manipulation device, the monitoring system traveling with the manipulation device, the monitoring system also having a camera which is secured to the gripper arm or which is mounted on the movable transport device for producing remote images and a location system having at least one transmitter and at least one receiver, the receiver being mounted on the movable transport device and being constructed in such a manner that it produces an alarm signal if the at least one transmitter falls below a minimum distance relative to the receiver.

2. Laboratory system according to claim 1, wherein at least one handling device is constructed so as to be movable.

3. Laboratory system according to claim 1, wherein the transport device (1) is constructed so as to be self-propelling.

4. Laboratory system according to claim 1, wherein the monitoring system has the camera for producing remote images, the camera configured to take a static image capture and new image capture, the monitoring system switching off the manipulation device when deviations between the static image capture and the new image capture are recognized.

5. Laboratory system according to claim 1, wherein the monitoring system has the location system having at least one transmitter and at least one receiver.

6. Laboratory system according to claim 1, wherein the transport path is a track that the transport device, at least one manipulation device with the gripper arm and samples move along between the at least two handling devices.

7. Laboratory system according to claim 1, wherein the electrical current and/or power monitoring device is a redundant electrical current and/or power monitoring device.

* * * * *